United States Patent
Urso

[11] Patent Number: 6,063,757
[45] Date of Patent: May 16, 2000

[54] WOUND TREATMENT METHOD WITH NERVE GROWTH FACTOR

[76] Inventor: Richard G. Urso, 6644 Rutgers Ave., Houston, Tex. 77005-3853

[21] Appl. No.: 08/753,642

[22] Filed: Nov. 27, 1996

Related U.S. Application Data

[63] Continuation-in-part of application No. 60/007,698, Nov. 29, 1995.

[51] Int. Cl.[7] .............................. A01N 37/18; A61K 38/00
[52] U.S. Cl. .............................. 514/2; 514/866; 514/912; 514/928; 424/85.1
[58] Field of Search ................................ 514/2, 866, 912, 514/928; 530/351; 924/85.1

[56] References Cited

U.S. PATENT DOCUMENTS

| | | |
|---|---|---|
| 4,287,184 | 9/1981 | Young . |
| 4,818,540 | 4/1989 | Chien et al. . |
| 5,169,762 | 12/1992 | Gray et al. . |
| 5,272,135 | 12/1993 | Takruri . |
| 5,401,510 | 3/1995 | Robertson et al. . |
| 5,427,778 | 6/1995 | Finkenaur . |

FOREIGN PATENT DOCUMENTS

| | | |
|---|---|---|
| 0121338 | 10/1984 | European Pat. Off. . |
| 0190 018B1 | 8/1986 | European Pat. Off. . |
| 0140 998B1 | 11/1989 | European Pat. Off. . |
| WO 86/02271 | 4/1986 | WIPO . |

OTHER PUBLICATIONS

Bocchini et al., "The Nerve Growth Factor: Purification As A Thirty Thousand Molecular Weight Protein", *Proc. Nat. Acad. Sci. USA* 64:787–794 (1969).

Davies "Neurotropic Factor Bioassay Using Associated Neurons" in *Nerve Growth Factors*, R.A.Rush, Ed., John Wiley & Sons Ltd., pp. 95–109 (1989).

Kitamura, et al. "Establishment and Characterization of a Unique Human Cell Line that Proliferates Dependently on GM–CSF, IL–3, or Erythropoietin" *J. Cell Physiology* 14:323–334 (1989).

Levi–Montalcini, "The Nerve Growth Factor Thirty Five Years Later" *In Vitro Cell. Devel. Biol.* 23:227–238 (1987).

Ullrich et al., "Human β–Nerve Growth Factor Gene Sequence Highly Homologous to that of Mouse" *Nature* 303:821–825 (1983).

Gener–Galbis et al., "The effect of NFG on corneal wound healing in rabbit" *Invest Opthalmol Vis Sci*(1993) 34(1315):abstract.

Lambiase, et al., "Tropical treatment with nerve growth for corneal neurotrophic ulcers" The New England Journal of Medicine (1998) 338(17):1174–1180.

Leitzel, et al., "Failure of nerve growth factor to enhance wound healing in the hamster" *Journal of Neuroscience Research* (1982) 8:413–417.

Barnett et al. *Exp. Neurol* 110 (1990) 11–24 Jackowski et al *Br. J. Neurosurgery* 9(1995) 303–317.

*Primary Examiner*—Patricia A. Duffy
*Attorney, Agent, or Firm*—Morrison & Foerster LLP

[57] ABSTRACT

A method is provided for healing chronic wounds in a subject, particularly wounds which exhibit poor vascularization and sensory loss. The treatment method involves administering a therapeutically effective amount of β-NGF to the subject to heal the wound. Compositions containing β-NGF for use in the wound healing methods are provided.

13 Claims, 1 Drawing Sheet

```
                  M   S   S   S   H   P   I   F   H   R   G   E   F   S   V   C
AAGCTTACCTGCCATGTCATCATCCCATCCCATCTTCCACAGGGGCGAATTCTCGGTGTG
HindIIIBspMI                                        EcoRI
TTCGAATGGACGGTACAGTAGTAGGGTAGGGTAGAAGGTGTCCCCGCTTAAGAGCCACAC
         10        20        30        40        50        60

D   S   V   S   V   W   V   G   D   K   T   T   A   T   D   I   K   G   K   E
TGACAGTGTCAGCGTGTGGGTTGGGGATAAGACCACCGCCACAGATATCAAGGGCAAGGA
                                                 EcoRV
ACTGTCACAGTCGCACACCCAACCCCTATTCTGGTGGCGGTGTCTATAGTTCCCGTTCCT
         70        80        90       100       110       120

V   M   V   L   G   E   V   N   I   N   N   S   V   F   K   Q   Y   F   F   E
GGTGATGGTGTTGGGAGAGGTGAACATTAACAACAGTGTATTCAAACAGTACTTTTTTGA
                                           ScaI
CCACTACCACAACCCTCTCCACTTGTAATTGTTGTCACATAAGTTTGTCATGAAAAAACT
        130       140       150       160       170       180

T   K   C   R   D   P   N   P   V   D   S   G   C   R   G   I   D   S   K   H
GACCAAGTGCCGGGACCCAAATCCCGTCGACAGCGGGTGCCGGGGCATTGACTCAAAGCA
                                AccI
CTGGTTCACGGCCCTGGGTTTAGGGCAGCTGTCGCCCACGGCCCCGTAACTGAGTTTCGT
        190       200       210       220       230       240

W   N   S   Y   C   T   T   H   T   F   V   K   A   L   T   M   D   G   K
CTGGAACTCATATTGTACCACGACTCACACCTTTGTCAAGGCGCTGACCATGGATGGCAA
                                                        NcoI
GACCTTGAGTATAACATGGTGCTGAGTGTGGAAACAGTTCCGCGACTGGTACCTACCGTT
        250       260       270       280       290       300

Q   A   A   W   R   F   I   R   I   D   T   A   C   V   C   V   L   S   R   K
GCAGGCTGCCTGGCGGTTTATCCGGATAGATACGGCCTGTGTGTGTGTGCTCTCTAGAAA
                BspMII                                      XbaI
CGTCCGACGGACCGCCAAATAGGCCTATCTATGCCGGACACACACACGAGAGATCTTT
        310       320       330       340       350       360

A   V   R   *   *
GGCTGTGAGATGATAAGGATCCTAATTC
                BaaHI
CCGACACTCTACTATTCCTAGGATTAAG
        370       380
```

Figure 1

WOUND TREATMENT METHOD WITH NERVE GROWTH FACTOR

CROSS REFERENCE TO RELATED APPLICATION

This application is a continuation-in-part of provisional application 60/007,698, filed on Nov. 29, 1995, which is hereby incorporated herein by reference in its entirety.

TECHNICAL FIELD

This invention relates to the field of wound treatment methods.

BACKGROUND ART

The treatment of chronic wounds has continually been a challenge to the medical profession. It is often very difficult to achieve wound healing in patients, and health professionals have resorted to managing wounds rather than being able to achieve healing and recovery.

Eyes are subject to chronic wounds and there have been prior attempts in the art to address these problems. Corneal epithelial defects generally heal within 24 to 48 hours. However, certain conditions can predispose the cornea to delayed healing or even continuous epithelial breakdown. For example, in photo refractive keratectomy (PRK) the cornea typically takes five to seven days to reepithelialize. Subepithelial haze occurs more commonly in patients with slower reepithelialization, and patients with decreased corneal sensation due to cranial nerve $V_f$ dysfunction suffer from persistent corneal epithelial defects that often lead to blindness. Patients who undergo penetrating keratoplasty often have difficulty with reepithelialization of the cornea. Reepithelialization of the cornea can be enhanced by patching of the eye and by providing adequate lubrication for the cornea in the form of drops and ointment. Many topical agents can delay or be toxic to the corneal epithelium. Numerous pharmacologic therapies have been advocated (sodium citrate and collagenase inhibitors) as enhancing reepithelialization of the cornea; however, success has been limited.

With regard to chronic wounds on areas of the body other than the eye, there is often associated microvascular disease i.e. poor vascular supply. Patients then suffer from poor oxygen flow to the tissues. It has been found that oxygen treatment in a hyperbaric oxygen chamber does provide for enhancement of healing. Decubitus ulcers, also known as pressure sores or bedsores, have classically been thought to be due to pressure on bony prominences of the body decreasing blood supply to the overlying skin, resulting in epithelial breakdown. This is especially common on the sacral area and buttocks. Decubitus ulcers are managed by preventing pressure in the areas prone to breakdown by turning the bedridden patient at regular intervals and by removing any toxic substance (eg. urine) from the particular area affected. There are other wounds as well which are reportedly caused by vascular problems, and recommended treatment has been to surgically revascularize the tissues. Little consideration is given to the role of sensory loss and its effect on maintaining an intact epithelium.

Other previously described methods of treating wounds have focussed on the use of epidermal growth factor (EGF), transforming growth factor (TGF), and fibroblast gowth factor (FGF). TGF binds to the same cell surface receptor as EGF. For treatment methods using EGF, see, e.g., PCT WO 86/02271 and EP 0140 998. EP 190 018 describes the use of TGF for the treatment of epithelial wounds and stromal wounds. These agents have turned out to be relatively ineffective in the management of chronic wounds.

U.S. Pat. No. 4,287,184 to Young describes using a form of NGF having a molecular weight of 116,000, in an experiment to heal a skin wound in mice. Refering to his invention, Young states that "the wound healing effect of the NGF of this invention is not observed with other forms of NGF, eg. 2.5S NGF." [col. 3, lines 44–46].

Despite the attempts to manage chronic wounds, to date no treatment is universally effective. Patients that do not respond to conventional therapies over long periods of time may suffer from continued chronic breakdown. In addition, the conventional therapies may require considerable periods of therapy, resulting in patients being without eyesight or being disabled due to chronic wounds for extended periods of time. Finally, the popularity of new eye operations designed to correct vision defects have resulted in a new population of eye patients who will need to undergo periods of recovery from epithelial disruption.

Thus, there remains a need for a more effective method for treating chronic wounds which will aid wound healing in the eye and and in other areas of the body.

The present invention satisfies this need and provides other advantages as well.

SUMMARY OF THE INVENTION

The present invention provides a method for healing a chronic wound in a subject by administering a therapeutically effective amount of β-NGF to the subject. The method is particularly suitable for treating wounds characterized by poor vascularization and/or decreased sensation. The method involves administering β-NGF at a concentration of 0.1–1000 ng/ml.

One aspect of the invention is a method of treating a chronic corneal wound by administering a therapeutically effective amount of β-NGF to the subject presenting the wound. The corneal wound is treated by topical administration of β-NGF formulated at a concentration of about 10–100 ng/ml.

Also provided by the invention is a method of treating a chronic cutaneous wound in a subject by administration β-NGF to the wound in an amount therapeutically effective to heal the wound. In a specific embodiment, β-NGF is administered topically to the wound at a concentration of about 100 ng/ml.

The invention also provides a composition for healing a chronic wound, wherein the composition contains a therapeutically effective amount of β-NGF and a physiologically acceptable carrier.

BRIEF DESCRIPTION OF THE DRAWINGS

FIG. 1 depicts the nucleotide sequence (SEQ ID NO.1), top strand; SEQ ID NO.3, bottom strand and amino acid sequence (SEQ ID NO. 2) of nerve growth factor beta (NGF-β) which was disclosed in FIG. 2B (boxed region) of Ullrich et al., *Nature* 303:821–825 (1983) and U.S. Pat. No. 5,169,762. The first Met is used as an initiation codon.

DETAILED DESCRIPTION FOR CARRYING OUT THE INVENTION

The present invention provides a method for healing chronic wounds by administering a therapeutically effective amount of β-nerve growth factor (β-NGF) to the subject suffering from the wound. The method of the invention is particularly useful for treating and healing chronic wounds that are characterized by poor vascularization and/or decreased sensation, such as present in a corneal wound or a cutaneous wound.

As presently demonstrated, administration of β-nerve growth factor to human subjects can greatly aid in regeneration of epithelial cells. Advantageously, the present method was effective in healing wounds that did not respond to conventional therapies. In addition, the wound treatment procedure is simple, non-invasive, achieves rapid healing (as quickly as one day), and is effective in low concentrations of β-NGF (10–100 ng/ml, less than 2 ng /dose), thus minimalizing the possibility of side effects.

Nerve growth factor is a neurotropic protein that plays a critical role in the development and maintenance of sympathetic and embryonic sensory neurons. Nerve growth factor isolated from male mouse submaxillary gland consists of three types of subunits, α, β and γ, which noncovalently interact to form a 7S, ~130 kD-molecular weight complex (Ullrich et al. Nature 303: 821–825 (1983)). The β subunit called β-NGF or 2.5S NGF, is that which has the biological activity for cell proliferation and is the subunit useful in the present invention. β-nerve growth factor (β-NGF) has been described in the literature. For a review of NGF, see Levi-Montalcini, In Vitro Cell. Devel. Biol. 23:227–238 (1987). The human β-NGF gene encodes a large polypeptide of 307 amino acid residues which, upon cleavage, gives rise to a 118-amino acid mature β-NGF subunit protein. The mature mouse β-NGF is also 118 amino acids long. In solution, β-NGF exists as a non-covalently linked homodimer (2.5S NGF) and has a molecular weight of about 26kD. Human β-NGF is highly homologous (90% homology) at the amino acid level to the mature mouse and rat β-NGF and exhibits cross-species activity (Ullrich et al. (1983) Nature 303: 823; U.S. Pat. No. 5,169,762, col. 9, line 7). β-NGF useful in this invention will refer to this non-covalent homodimer form which can be isolated from naturally occurring sources or prepared biosynthetically such as by recombinant methods.

For practicing the wound treatment method of the present invention, suitable sources of β-NGF include human, rodent, bovine and porcine NGF. For administration to humans, the preferred source of β-nerve growth factor is human β-NGF, preferably, recombinant human β-nerve growth factor (rhβ-NGF). A rhβ-NGF is described in U.S. Pat. No. 5,169,762 which is incorporated herein by reference. The amino acid sequence (SEQ ID NO.2) of recombinant human nerve growth factor is shown in FIG. 1. β-NGF is commercially available. For example, R&D Systems Inc. of Minneapolis, Minn. (Catalog No. 256-GF) provides a 120 amino acid residue mature rhβ-NGF having a predicted molecular mass of approximately 13.2 kD (monomer mass). This rhβ-NGF is sold in sterile, lyophilized form. In solution, β-NGF exists as a non-disulfide linked homodimer.

The biological activity of this rhβ-NGF as measured in a cell proliferation assay (Kitamura, et al. *J Cell Physiology* 14:323–334 (1989)) showed an $ED_{50}$ of 0.8 to 1.5 nanograms per ml. The activity as measured by its ability to support the survival and neurite outgrowth of cultured embryonic chick dorsal root ganglia (Davies "Neurotropic Factor Bioassay Using Associated Neurons" in *Nerve Growth Factors*, R. A. Rush, Ed., John Wiley & Sons Ltd., pp. 95–109) gave an $ED_{50}$ of 0.5 to 1.0 nanograms per ml.

Nerve growth factor isolated from other species, example, from mouse, can also be used in treating human subjects since there is species cross-reactivity and since the human and rodent proteins are highly homologous. Mouse β-NGF (2.5S NGF) is purified typically by chromatography, as a homodimer of 26,000 daltons. Mouse 2.5S β-NGF is available from the following: Pierce, Rockford, Ill.; Upstate Biotechnology, Inc., Lake Placid, New York; GibcoBRL, Grand Island, N.Y. The biological activity and purity of the commercial β-NGF will generally be specified by the manufacturer. cDNAs encoding human and mouse β-NGF are available and can be used in a suitable expression system to express and isolate the protein.

The procedure for isolation of nerve growth factor is provided in Bocchini et al., The Nerve Growth Factor: Purification As A Thirty Thousand Molecular Weight Protein, Proc. Nat. Acad. Sci.USA 64:787–794 (1969).

It is expected that certain modifications can be made to the nerve growth factor while retaining the desired activity. Recombinantly produced β-NGF can contain more or less than 118 amino acids in the monomer polypeptide as long as the biological activity and particularly the wound healing activity of the protein is maintained. For example, β-NGF polypeptides that are truncated or or that contain certain amino acid changes that do not alter the wound healing activity of the growth factor or introduce any undesirable effects in the patient, are usable in this invention. β-NGF may also be synthesized as part of a fusion protein to facilitate isolation and identification of the NGF.

The present methods are particularly useful for treating wounds in areas that are poorly vascularized and poorly innervated. For example, the development of chronic wounds secondary to compromised blood flow and decreased sensation from normal is a well known complication of patients with diabetes mellitus. Patients who suffer from hemiplegia have decreased sensation due to spinal cord injury and decreased tissue oxygenation secondary to prolonged pressure over bony prominences. The cornea serves as a model for certain chronic wounds which exhibit both sensory and vascular problems. This is based on the fact that the cornea is naturally avascular and that sensory loss, coupled with poor vascularization, leads to epithelial breakdown. Thus, chronic wounds that can be treated by the present method include, but are not limited to, wounds caused by or associated with the following conditions: corneal epithelial defects which can result from varying causes, eg. from severing or disruption of the first branch of the trigeminal nerve, or from chemical burns such as acid or alkali burns, or as a complication of viral infections eg. ophthalmicus zoster or herpes keratitis; epithelial breakdown following penetrating keratoplasty; delayed healing following photorefractive keratectomy (PRK); diabetic foot ulcers; decubitus ulcers; and venous stasis ulcers. These wounds are present in the eye or in other areas of the body, eg. the lower leg and foot, sacral region, buttocks.

One embodiment of the invention is a method of healing a corneal wound or defect by administering a therapeutically effective amount of β-NGF to the subject presenting the wound. In another embodiment, the present method is applied to the treatment of cutaneous wounds.

The present methods of healing chronic wounds will typically be practiced in a human subject or patient but can be applied to other mammals including but not limited to horses, dogs, cats and other pets.

In accordance with the treatment method of the present invention, one would administer to the subject or patient suffering from the wound, an amount of β-NGF therapeutically effective to heal the wound. For treatment of eye or corneal wounds, a therapeutically effective amount of β-NGF is the amount which will provide for an observable healing effect in the epithelium within twenty-four to seventy-two hours. The observable effect is improved clarity of the epithelium and/or a decrease in size of the epithelial defect. The healing effect on the epithelium in the eye can be observed using the slit lamp microscope which is a standard instrument used by ophthalmologists. In areas other than the eye, such as a diabetic foot ulcer or a decubitus ulcer, the therapeutically effective amount is the amount that will produce a beneficial healing effect visible to a physician within 3–7 days, generally within about 72 hours. The beneficial healing effect can be determined by daily measurement of the width, length and depth of the wound in millimeters, using a ruler. Preferably, the amount of β-NGF administered is sufficient to reduce the size of the wound by at least 50%, preferably, by 75% and even more preferably, by 90–100%.

The amount to produce a desired therapeutic effect will vary in part with the type and extent of disease or injury in the particular subject at issue, biological activity or degree of purity of NGF employed, the manner and frequency of administration of the drug, the type of formulation and carrier used, overall health of the individual being treated and the like. It would be expected that a subject having a minor injury could be benefited by nerve growth factor in a minor amount to speed recovery of the epithelial trauma. With greater epithelial disruption, it is expected that a greater amount of nerve growth factor may be desirable to provide the desired therapeutic effect. The therapeutically effective amount of NGF in the compositions used to treat cutaneous wounds will also vary depending on such factors as condition and age of the skin. The precise amount for use with any particular patient can be determined by those of skill in the pharmaceutical art taking into consideration these factors and the present disclosure.

Thus far, no toxic effects have been observed in patients treated with β-NGF at 100 ng/ml or even 1000 ng/ml. Greater amounts of nerve growth factor may be beneficial and tolerated. A maximum dosage that can be tolerated without toxicity can be determined by using standard techniques familiar to one of skill in this art. Patients can be monitored for the following signs of toxicity. Toxic reactions that may occur with application of the drug to the eye include injection of the sclera, papillary or follicular reactions of the conjunctiva, allergic dermatitis and intraocular inflammation, all of which can be detected with the slit lamp. With dermatologic application of β-NGF, toxicity might be expected to be largely localized because of the application process as well as the small amounts of drug used. Local erythema, edema and even scarring are possible side effects. Systemic abnormalities including anaphylaxis are unlikely and have not been observed with the present treatment method.

The minimum amount of nerve growth factor to use would be dependent on the condition of the patient at the outset of therapy. As the working examples below demonstrate, a ten nanograms per ml solution of β-NGF applied in the amount of one drop per hour for several days provided an observarble and measurable therapeutic effect. The minimum dosage necessary to provide desirable therapeutic effects can be determined by techniques well known in the art. Typically, the subject will be treated with β-NGF at a concentration of 0.1 ng/ml to 1000 ng/ml, more typically at about 1–100 ng/ml, even more preferably, at 10–100 ng/ml. The most preferred concentration of β-NGF for treatment is at 100 ng/ml. Preferably a β-NGF composition is administered in at least two but no more than about 15 doses per day. The number of doses can be less when a sustained or delayed release form is used. The dosage and number of applications per day can subsequently be reduced upon noticeable improvement and healing of the wound. Dosage can be reduced by at least 2-fold and in some cases, as much as 10-fold. β-NGF will be administered in this manner for at least 1 day, generally 2–7 days to achieve wound healing. Dermatologic wounds would be expected to heal more slowly.

β-NGF will typically be administered with a physiologically acceptable carrier or diluent. For the purpose of this invention, a physiologically acceptable carrier is one that does not cause an adverse physical reaction upon administration and one in which NGF is sufficiently soluble to deliver a therapeutically effective amount of the compound. The form of carrier suitable will partly depend on the type and location of the wound and the route of administration. Desirably, the carrier should allow the β-NGF to be applied to the wound for an extended period of time.

In one embodiment, the physiologically acceptable carrier is suitable for topical application to mammalian tissue. For ocular application, the nerve growth factor can be prepared in a physiologically acceptable carrier or diluent which is ionically compatible with the eye, sterile, and non-toxic. Isotonic solutions for ocular application include, but are not limited to, saline and phosphate buffered saline, balanced salt solution (BSS) and artificial tears. β-NGF sold commercially in lyophilized form can be reconstituted with these physiologically acceptable diluents.

For treatment of skin wounds, it may be desirable to administer the NGF in admixture with a topical pharmaceutically or cosmetically acceptable carrier. The topical pharmaceutically acceptable carrier is any substantially non-toxic carrier conventionally usable for topical administration of pharmaceuticals in which NGF will remain stable and bioavailable when applied directly to skin or epithelial surfaces. Carriers such as those known in the art effective for penetrating the keratin layer of the skin into the stratum corneum may be useful in delivering β-NGF to the area of interest. Such carriers include liposomes. NGF can be dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, buffered saline, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, alcohols, polyols, and the like. The carrier can be a water miscible carrier composition. Such water miscible, topical pharmaceutically acceptable carrier composition can include those made with one or more appropriate ingredients set forth above but can also include sustained or delayed release carriers, including water containing, water dispersible or water soluble compositions, such as liposomes, microsponges, microspheres or microcapsules, aqueous base ointments, water-in-oil or oil-in-water emulsions, gels or the like.

Because dermatologic conditions to be treated may be visible, the topical carrier can also be a topical cosmetically acceptable carrier. The topical cosmetically acceptable carrier will be any substantially non-toxic carrier conventionally usable for topical administration of cosmetics in which NGF will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Topical cosmetically acceptable carriers may be similar or identical in nature to the above described topical pharmaceutically acceptable carriers. The compositions can contain other ingredients conventional in cosmetics including perfumes, estrogen, vitamins A, C or E, alpha-hydroxy or alpha-keto acids such as pyruvic, lactic or glycolic acids, lanolin, vaseline, aloe vera, methyl or propyl paraben, pigments and the like.

It may be desirable to have a delivery system that controls the release of NGF to the wound and adheres to or maintains itself on the wound for an extended period of time to increase the contact time of NGF on the wound. Sustained or delayed release of NGF provides a more efficient administration resulting in less frequent and/or decreased dosage of NGF and better patient compliance. Examples of suitable carriers for sustained or delayed release in a moist environment include gelatin, gum arabic, xanthane polymers. Pharmaceutical carriers capable of releasing β-NGF when exposed to any oily, fatty, waxy, or moist environment on the area being treated, include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Controlled delivery systems are described, for example, in U.S. Pat. No. 5,427,778 which provides gel formulations and viscous solutions for delivery of growth factors to a wound site. Gels have the advantages of having a high water content to keep the wound moist, the ability to absorb wound exudate, easy application and easy removal by washing. Preferably, the sustained or delayed release carrier is a gel, liposome, microsponge or microsphere.

β-NGF can also be administered in combination with other pharmaceutically effective agents including, but not limited to, antibiotics, other wound healing agents, and antioxidants.

The route of administration of β-NGF will depend on the site of the wound and the type and extent of the injury. Any suitable application method can be used as long as an effective amount of β-NGF is able to reach the areas which require regeneration for wound healing to occur. Routes of administration include, but are not limited to, topical, transdermal and parenteral. Typically, β-NGF will be administered by topical or transdermal application.

Topical administration is accomplished via a topically applied solution, cream, gel or other suitable formulation containing a therapeutically effective amount of β-NGF. β-NGF can be mixed with a pharmaceutically acceptable cream, applied to the wound, and covered with an occlusive dressing. Alternatively, the wound area can be irrigated or soaked with a solution of β-NGF. The solution will be applied two to twelve times per day.

For transdermal application, β-NGF is formulated in a composition capable of allowing the NGF to penetrate the skin and site of the wound. Such compositions are applied directly to the skin or incorporated into a protective carrier such as a transdermal or "patch" device. The NGF formulations for transdermal administration can be used to coat the fibers of an absorbent gauze dressing to form a wound healing bandage which can then be applied to the wound such that the β-NGF composition contacts the wound. Suitable formulations for transdermal applications such as a cream, ointment, gel, etc. are described, for example, in the Physician's Desk Reference. Examples of suitable transdermal devices are described, for instance, in U.S. Pat. No. 4,818,540.

Parenteral routes of administration include, but are not limited to, subcutaneous injection, intravenous or intramuscular injection, into the site of the localized wound.

One embodiment of the invention is a method of treating a corneal wound in a subject by administering β-NGF to the subject in an amount therapeutically effective to heal the wound. Applying a solution of β-nerve growth factor in drop form directly into the eye was found to be effective in healing corneal wounds. Preferably, the β-NGF is administered with a physiologically acceptable carrier such as balanced salt solution or artificial tears. The subject suffering from a corneal wound is treated by topical application of an aqueous solution of β-NGF wherein the β-NGF is present at a concentration of 0.1 to 1000 ng/ml. Preferably, the β-NGF is at a concentration of about 10–100 ng/ml, even more preferably, at 100 ng/ml. Preferably the β-NGF composition is administered in at least two doses and no more than about 15 doses per day, or less when a sustained or delayed release form is used. One drop of the β-NGF composition can be conveniently be applied to the eye using a standard eye dropper, once every 1–2 hours for about 6–12 times a day, preferably 8 times a day. One drop of a 100 ng/ml solution contains approximately 1.6 ng of β-NGF. The drug concentration and number of applications can be reduced upon noticeable improvement and healing of the wound. In one embodiment, rhβ-NGF at a concentration of 100 ng/ml in balanced salt solution is topically administered to the eye at a dosage of one drop per application for about 8 times a day. Following this treatment regimen, healing will usually occur after one to seven days of treatment although certain patients may require several weeks of such treatment. In some rarer circumstances, continuous treatment will be required to prevent recurrence of epithelial breakdown. Usually, continuous administration will be at a reduced dosage than the initial treatment regimen.

Also provided by the invention is a method of treating a chronic cutaneous wound in a subject by administering β-NGF to the subject in an amount therapeutically effective to heal the wound. Before initiating β-NGF treatment, the general condition and size of the wound will be noted. Reduction in the size of the wound upon treatment will be visible to the eye. Formulations of β-NGF suitable for applying to cutaneous wounds are as described above and include creams, ointments, gels and solutions of β-NGF. In one embodiment, the cutaneous wound is a diabetic foot ulcer or a venous stasis ulcer. The therapeutically effective amount of β-NGF for healing a cutaneous wound will vary with the type of formulation used to deliver the active agent but β-NGF will generally be at a concentration of 0.1 ng/ml to 1000 ng/ml. Preferably, β-NGF is administered at a concentration of 100 ng/ml. The dosage can be reduced upon improvement in the condition of the wound. The β-NGF composition will generally be applied topically in an amount sufficient to cover the entire surface area of the wound, 1–5 times daily, preferably twice daily. Improvement in the condition of the defect or lesion will usually be observable in a week. Complete healing of cutaneous wounds may be achieved in several days to several weeks. With more extensive and long existing wounds, healing may require one to several months. In one embodiment, a diabetic foot ulcer and a venous stasis ulcer is treated by application of a solution of rhβ-NGF at a concentration of 100 ng/ml, twice daily.

The invention further provides the use of β-NGF-containing compositions for treating and healing chronic wounds. The compositions will contain at least a therapeutically effective amount of NGF and may contain at least one physiologically acceptable carrier. The β-NGF will generally be present at a concentration of 0.1 ng/ml to 1000 ng/ml, more typically at 10 ng/ml to 100 ng/ml, and preferably, at 100 ng/ml. Suitable physiologically acceptable carriers are as disclosed above.

β-NGF compositions of the present invention may also contain other pharmaceutically effective agents including, but not limited to, antibiotics, other wound healing agents, and antioxidants. Compositions of the present invention may further comprise various formulatory ingredients, such as antimicrobial preservatives and tonicity agents. Humectants may be included to promote lubrication and to preserve the natural tear physiology.

Adjuvants or pharmaceutically inactive ingredients can be added to the compositions for ophthalmic use to further stabilize, preserve and maintain the composition. The adjuvants added to the composition are those which are typically added to aqueous ophthalmic preparations, for example, sodium chloride can be added at a concentration of about 0.9% w/v or less to assist in making the ophthalmic composition physiologically isotonic. Other components that optionally can be included in the composition include a buffer system to maintain a pH of optimum stability. Carrier proteins such as serum albumin can also be added, generally at 0.1% or more.

In one embodiment, the wound healing compositions of the present invention are formulated for topical application to the eye. The compositions for topical ophthalmic application can be formulated in various forms including solutions, suspensions, emulsions and gels. Prefererred ophthalmic formulations are aqueous solutions.

Compositions suitable for transdermal application will be in a form such as a cream, rinse, gel, etc. that is capable of allowing NGF to penetrate the skin and site of the wound.

The following clinical examples are intended to be exemplary of the invention, but not limiting thereof.

EXAMPLES

Example 1

A patient who had suffered severing of the trigeminal nerve and suffering from a lack of sensory sensation in the eye, developed epithelial disruption. The patient was treated for six months with standard therapy including a suture tarssrhaphy as well as lubrication with ointment and tear substitutes without success. After six months, the condition of the patient's epithelium was not improved. Corneal stroma was thinning.

The patient was treated with recombinant human β-NGF obtained from the R&D Systems Inc. of Minneapolis, Minn. (Catalog No. 256-GF), which was diluted in buffered salt solution to a concentration of 100 nanograms per milliliter. One drop of this solution was administered to the eye every hour, or approximately ten to twelve times per day. After treatment for three days, ninety percent of the defect had healed. Before treatment, the epithelial defect was oval in shape and measured 8×5 mm in size. Within 3 days of treatment, the lesion was reduced to 4×3 mm. After 10 days of treatment, the lesion measured 1×2 mm.

The treatment regimen was then changed to administration of drops every two hours and the dosage reduced to ten nanograms per ml. The epithelial layer continued to show improvement and was completely healed by 2 weeks.

Example 2

A patient with epithelial trauma of unknown etiology was experiencing decreased sensation and poor healing of the epithelium for four weeks. The patient was placed on a therapy of ten nanograms per ml β-NGF at a dosage of one drop every hour, 8 times daily. The patient experienced dramatic improvement of the epithelium and complete healing in four days.

Example 3

The patient had had a corneal transplant six weeks prior to seeking treatment for epithelial disruption. The epithelial cells had not healed following the surgery. The patient was treated topically with a regimen of β-NGF at a dosage of ten nanograms per ml, one drop every hour, for a total of 8 times per day. Within one day, the epithelial layer exhibited vast improvement. With continued therapy, the epithelial layer appeared almost normal within a week's period of time.

Example 4

A patient with a history of ophthalmicus zoster and decreased corneal sensation developed a non healing corneal epithelial defect and stromal thinning. The patient did not respond well to conventional therapy including lubricants, ointments and patching. After 3 months of no improvement, treatment with rhβ-NGF was initiated. The patient was administered rhβ-NGF at a dose of 100 ng/ml, one drop per application, 10 times daily. Before β-NGF treatment, the defect was oval in shape and measured 7 mm×5 mm. The lesion was reduced to a size of 3.5 mm×3 mm in 4 days of treatment, and further reduced to 2.0 mm×1.5 mm after 10 days. The wound was completely healed in 3 weeks.

Example 5

A 35 year old male suffered an alkali burn to the left eye. The patient had a 90% epithelial defect which did not respond to conventional therapy including tears, lubricants, patching, tarssorhapy or a collagenase inhibitor. Treatment with rhβ-NGF was initiated 5 months after the unusual injury. The patient was started on rhβ-NGF at 1000 ng/ml, eight times daily. Initially, the defect measured 9.5 mm×9.5 mm. In 3 days of treatment, the defect measured 8 mm×8 mm. The dosage was then reduced to 100 ng/ml and treatment continued at eight times daily. At one week, the size of the defect measured 7.0 mm×7.5 mm. At 2 weeks, the lesion was 6 mm×5 mm. The number of applications at 100 ng/ml was reduced to 4 times daily. At 4 weeks, the defect was 3 mm×4 mm. At 6 weeks the defect had shrunk to 1 mm×2 mm and at eight weeks it was completely healed.

Example 6

A 68 year old male had a history of herpes keratitis which subsequently necessitated a corneal graft in the right eye. Post operatively, the patient had a persistent epithelial defect which did not respond to conventional therapy. Attempts at lowering the steroid dose also did not improve the epithelial defect. Collagenase inhibitors had no appreciable effect. The defect measured 7 mm×6 mm prior to initiating the growth factor treatment. rhβ-NGF at a dose of 100 ng/ml was administered in drop form, 6 times daily to the affected eye.

Within 1 week the epithelial defect was 4 mm×3 mm. By 17 days, the corneal epithelium was completely intact. The patient needed to be maintained on 2 drops daily to prevent recurring epithelial breakdown.

Example 7

A 52 year old white female with a 30 year history of diabetes developed a diabetic foot ulcer near the plantar surface of her foot. The ulcer measured 1.5 cm×1 cm and was 0.5 cm deep. The ulcer had resisted therapy with repeated duoderm foot dressings and had been present for more than one year. Treatment with rhβ-NGF was initiated. A buffered salt solution of rhβ-NGF at a concentration of 100 ng/ml was applied twice daily, in an amount sufficient to cover the area of the wound. The size of the defect was notably improved and measured 1.3 cm×0.8 cm with 0.5 cm in depth. The patient exhibited slow but consistent improvement. At two and a half months, the lesion was completely healed.

Example 8

A 54 year old white female with a history of diabetes for approximately 20 years, suffered a diabetic foot ulcer that failed to respond to conventional therapy for more than 6 months. This patient was treated with rhβ-NGF at 100 ng/ml twice daily. The lesion was originally 1.5 cm×2.0 cm in size. Improvement was noted at 1 week at which point the defect measured 1.1 cm×1.6 cm. Within 1 month, the lesion was completely healed.

Example 9

A 64 year old white male with a history of venous stasis ulcers for 10 years in the right foot was presented. The patient had persistence of the two venous stasis ulcers despite numerous types of treatment including hyperbaric oxygen chamber. At the beginning of the treatment, the smaller defect measured 2 cm×1.5 cm and the larger defect was 3 cm×2.0 cm. Treatment with rhβ-NGF was started at a dose of 100 ng/ml twice daily. rhβ-NGF was applied in sufficient amount to cover the whole surface of the wound. Noticeable improvement was seen at 1 week when the defects then measured 1.8 cm×1.3 cm and 2.8 cm×1.8 cm, respectively. By 2 months, the smaller defect was completely reepithelialized and the larger defect was 50% healed at which time the patient discontinued therapy and was lost to follow up.

In all the above examples, the patients were treated with drops of β-NGF in solution form. However, as disclosed above, the drug can be prepared and administered in other suitable formulations.

As is apparent to those of skill in the art, various modifications and alterations to the above can be made without departing from the spirit and scope of the invention.

I claim:

1. A method for healing a chronic corneal or cutaneous wound in a subject, comprising topically or transdermally administering 2.5S β-NGF to a subject in an amount therapeutically effective to heal the wound.

2. The method of claim 1 wherein the corneal or cutaneous wound is characterized by poor vascularization, decreased sensation or a combination of poor vascularization and decreased sensation.

3. The method of claim 2 wherein the 2.5S β-NGF is administered in a physiologically acceptable carrier.

4. The method of claim 2 wherein the corneal or cutaneous wound is caused by a condition selected from the group consisting of diabetes, hemiplegia, severing or disruption of the first branch of the trigeminal nerve, chemical burns, viral infections, penetrating keraplasty, photoreactive ketatectomy, diabetic foot ulcer, decubitus ulcer, and venous stasis ulcer.

5. The method of claim 2 wherein the 2.5S β-NGF is human β-NGF.

6. The method of claim 5 wherein the β-NGF is recombinant human 2.5S β-NGF (rh2.5S β-NGF).

7. The method of claim 3 wherein 2.5S β-NGF is administered at a concentration of between 0.1 ng/ml to 1000 ng/ml of a stock solution of 2.5S β-NGF.

8. The method of claim 7 wherein 2.5S NGF is administered at a concentration of 10–100 ng/ml of a stock solution of 2.5S β-NGF.

9. The method of claim 1 wherein the 2.5S β-NGF is administered with a physiologically acceptable carrier.

10. The method of claim 9 wherein the physiologically acceptable carrier is balanced salt solution (BBS) or artificial tears.

11. The method of claim 8 wherein the 2.5S β-NGF is administered at a concentration of 100 ng/ml.

12. The method of claim 1 wherein the rh 2.5S β-NGF is at a concentration of 100 ng/ml in balanced salt solution, and is applied to the corneal wound at a dosage of one drop for about 8 times a day.

13. The method of claim 4 wherein 2.5S β-NGF in the form of rh2.5S β-NGF is applied topically twice daily in an amount sufficient to cover the area of the wound, at a concentration of 100 ng/ml.

* * * * *

UNITED STATES PATENT AND TRADEMARK OFFICE

CERTIFICATE OF CORRECTION

PATENT NO. : 6,063,757
DATED : May 16, 2000
INVENTOR(S) : Richard G. URSO

It is certified that error appears in the above-identified patent and that said Letters Patent is hereby corrected as shown below:

In column 15, line 20, after "human" add --2.5S--.

In column 15, line 21, after "the" add --2.5S--.

Signed and Sealed this

Third Day of April, 2001

NICHOLAS P. GODICI

*Attest:*

*Attesting Officer*  *Acting Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 388 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 14..370

(xi) SEQUENCE DESCRIPTION: SEQ ID NO:1:

```
AAGCTTACCT GCC ATG TCA TCA TCC CAT CCC ATC TTC CAC AGG GGC GAA         49
           Met Ser Ser Ser His Pro Ile Phe His Arg Gly Glu
            1               5                  10

TTC TCG GTG TGT GAC AGT GTC AGC GTG TGG GTT GGG GAT AAG ACC ACC         97
Phe Ser Val Cys Asp Ser Val Ser Val Trp Val Gly Asp Lys Thr Thr
         15                  20                  25

GCC ACA GAT ATC AAG GGC AAG GAG GTG ATG GTG TTG GGA GAG GTG AAC        145
Ala Thr Asp Ile Lys Gly Lys Glu Val Met Val Leu Gly Glu Val Asn
     30                  35                  40

ATT AAC AAC AGT GTA TTC AAA CAG TAC TTT TTT GAG ACC AAG TGC CGG        193
Ile Asn Asn Ser Val Phe Lys Gln Tyr Phe Phe Glu Thr Lys Cys Arg
 45                  50                  55                  60

GAC CCA AAT CCC GTC GAC AGC GGG TGC CGG GGC ATT GAC TCA AAG CAC        241
Asp Pro Asn Pro Val Asp Ser Gly Cys Arg Gly Ile Asp Ser Lys His
                 65                  70                  75

TGG AAC TCA TAT TGT ACC ACG ACT CAC ACC TTT GTC AAG GCG CTG ACC        289
```

```
Trp Asn Ser Tyr Cys Thr Thr Thr His Thr Phe Val Lys Ala Leu Thr
        80                  85                  90

ATG GAT GGC AAG CAG GCT GCC TGG CGG TTT ATC CGG ATA GAT ACG GCC      337
Met Asp Gly Lys Gln Ala Ala Trp Arg Phe Ile Arg Ile Asp Thr Ala
        95                  100                 105

TGT GTG TGT GTG CTC TCT AGA AAG GCT GTG AGA TGATAAGGAT CCTAATTC      388
Cys Val Cys Val Leu Ser Arg Lys Ala Val Arg
    110                 115
```

(2) INFORMATION FOR SEQ ID NO:2:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Ser Ser His Pro Ile Phe His Arg Gly Glu Phe Ser Val Cys
 1               5                  10                  15

Asp Ser Val Ser Val Trp Val Gly Asp Lys Thr Thr Ala Thr Asp Ile
            20                  25                  30

Lys Gly Lys Glu Val Met Val Leu Gly Glu Val Asn Ile Asn Asn Ser
        35                  40                  45

Val Phe Lys Gln Tyr Phe Phe Glu Thr Lys Cys Arg Asp Pro Asn Pro
    50                  55                  60

Val Asp Ser Gly Cys Arg Gly Ile Asp Ser Lys His Trp Asn Ser Tyr
65                  70                  75                  80

Cys Thr Thr Thr His Thr Phe Val Lys Ala Leu Thr Met Asp Gly Lys
                85                  90                  95

Gln Ala Ala Trp Arg Phe Ile Arg Ile Asp Thr Ala Cys Val Cys Val
                100                 105                 110

Leu Ser Arg Lys Ala Val Arg
        115
```

(2) INFORMATION FOR SEQ ID NO:3:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:3:

```
GAATTAGGAT CCTTATCATC TCACAGCCTT TCTAGAGAGC ACACACACAC AGGCCGTATC      60

TATCCGGATA AACCGCCAGG CAGCCTGCTT GCCATCCATG GTCAGCGCCT TGACAAAGGT     120

GTGAGTCGTG GTACAATATG AGTTCCAGTG CTTTGAGTCA ATGCCCCGGC ACCCGCTGTC     180

GACGGGATTT GGGTCCCGGC ACTTGGTCTC AAAAAAGTAC TGTTTGAATA CACTGTTGTT     240

AATGTTCACC TCTCCCAACA CCATCACCTC CTTGCCCTTG ATATCTGTGG CGGTGGTCTT     300

ATCCCCAACC CACACGCTGA CACTGTCACA CACCGAGAAT TCGCCCCTGT GGAAGATGGG     360

ATGGGATGAT GACATGGCAG GTAAGCTT                                        388
```